US010327709B2

(12) United States Patent
Heldt et al.

(10) Patent No.: US 10,327,709 B2
(45) Date of Patent: Jun. 25, 2019

(54) SYSTEM AND METHODS TO PREDICT SERUM LACTATE LEVEL

(71) Applicants: Massachusetts Institute of Technology, Cambridge, MA (US); The General Hospital Corporation, Boston, MA (US)

(72) Inventors: Thomas Heldt, Cambridge, MA (US); Max H. Dunitz, Redondo Beach, CA (US); George Cheeran Verghese, Newton, MA (US); Andrew Tomas Reisner, Newton, MA (US); Michael Filbin, Jamaica Plain, MA (US)

(73) Assignees: Massachusetts Institute of Technology, Cambridge, MA (US); The General Hospital Corporation, Boston, MA (US)

(*) Notice: Subject to any disclaimer, the term of this patent is extended or adjusted under 35 U.S.C. 154(b) by 273 days.

(21) Appl. No.: 15/236,114

(22) Filed: Aug. 12, 2016

(65) Prior Publication Data

US 2017/0042483 A1    Feb. 16, 2017

Related U.S. Application Data

(60) Provisional application No. 62/204,292, filed on Aug. 12, 2015.

(51) Int. Cl.
*A61B 5/021*    (2006.01)
*A61B 5/024*    (2006.01)
(Continued)

(52) U.S. Cl.
CPC ............ *A61B 5/7267* (2013.01); *A61B 5/021* (2013.01); *A61B 5/024* (2013.01);
(Continued)

(58) Field of Classification Search
CPC ... A61B 5/7267; A61B 5/02028; A61B 5/021; A61B 5/02108; A61B 5/024;
(Continued)

(56) References Cited

U.S. PATENT DOCUMENTS 6,804,551 B2    10/2004 Griffin et al.
7,972,296 B2 *    7/2011 Braig .................. A61B 5/1427
604/66
(Continued)

OTHER PUBLICATIONS

PCT/US2016/046915, dated Feb. 22, 2018, International Preliminary Report on Patentability.
(Continued)

*Primary Examiner* — Navin Natnithithadha
(74) *Attorney, Agent, or Firm* — Wolf, Greenfield & Sacks, P.C.

(57) ABSTRACT

A method to quantitatively predict a patient's serum lactate level, comprising measuring arterial blood pressure and heart rate from the patient, computing estimates of one or more cardiovascular parameters from the measured arterial blood pressure and heart rate, providing one or more classifiers that have been trained on a training data set including a reference set of arterial blood pressure, heart rate, and serum lactate levels and using the one or more classifiers to estimate the serum lactate level of the patient.

25 Claims, 12 Drawing Sheets

(51) Int. Cl.
| | |
|---|---|
| *A61B 5/00* | (2006.01) |
| *A61B 5/22* | (2006.01) |
| *A61B 5/02* | (2006.01) |
| *A61B 5/145* | (2006.01) |
| *G16H 50/30* | (2018.01) |

(52) U.S. Cl.
CPC ...... *A61B 5/02028* (2013.01); *A61B 5/02108* (2013.01); *A61B 5/14546* (2013.01); *A61B 5/222* (2013.01); *A61B 5/412* (2013.01); *A61B 5/4866* (2013.01); *A61B 5/7275* (2013.01); *A61B 5/7278* (2013.01); *A61B 5/742* (2013.01); *A61B 5/7405* (2013.01); *A61B 5/746* (2013.01); *G16H 50/30* (2018.01)

(58) Field of Classification Search
CPC ..... A61B 5/14546; A61B 5/222; A61B 5/412; A61B 5/4866; A61B 5/7275; A61B 5/7278; A61B 5/7405; A61B 5/742; A61B 5/746
USPC .............. 600/481, 483–486, 488, 490–503
See application file for complete search history.

(56) References Cited

U.S. PATENT DOCUMENTS

| | | | |
|---|---|---|---|
| 8,282,564 | B2 | 10/2012 | Parlikar et al. |
| 8,615,291 | B2 | 12/2013 | Moorman et al. |
| 8,798,704 | B2 | 8/2014 | McKenna |
| 8,852,094 | B2 | 10/2014 | Al-Ali et al. |
| 2009/0149724 | A1 | 6/2009 | Mark et al. |
| 2012/0306884 | A1 | 12/2012 | Parlikar et al. |

OTHER PUBLICATIONS

International Preliminary Report on Patentability dated Feb. 22, 2018 for Application No. PCT/US2016/046915.
Dellinger et al., Surviving sepsis campaign: International guidelines for management of severe sepsis and septic shock, 2012. Intensive Care Med. Feb. 2013;39(2):165-228. doi: 10.1007/s00134-012-2769-8. Epub Jan. 30, 2013.
Gultepe et al., From vital signs to clinical outcomes for patients with sepsis: a machine learning basis for a clinical decision support system. J Am Med Inform Assoc. Mar.-Apr. 2014;21(2):315-25. doi: 10.1136/amiajnl-2013-001815. Epub Aug. 19, 2013.
Hajjar et al., High lactate levels are predictors of major complications after cardiac surgery. J Thorac Cardiovasc Surg. Aug. 2013;146(2):455-60. doi: 10.1016/j.jtcvs.2013.02.003. Epub Mar. 18, 2013.
Ilic et al., Intraoperative volume restriction in esophageal cancer surgery: an exploratory randomized clinical trial. Croat Med J. Jun. 2015;56(3):290-6. doi: 10.3325/cmj.2015.56.290.
Jansen et al., Early lactate-guided therapy in intensive care unit patients: A multicenter, open-label, randomized controlled trial. Am J Respir Crit Care Med. Sep. 15, 2010;182(6):752-61. doi: 10.1164/rccm.200912-1918OC. Epub May 12, 2010.
Jones et al., Lactate clearance vs central venous oxygen saturation as goals of early sepsis therapy: A randomized clinical trial. JAMA. Feb. 24, 2010;303(8):739-46. doi: 10.1001/jama.2010.158. 17 pages.
Kellum et al., Release of lactate by the lung in acute lung injury. Chest. May 1997;111(5):1301-5.
Kruse et al., Blood lactate as a predictor for in-hospital mortality in patients admitted acutely to hospital: A systematic review. Scand J Trauma Resusc Emerg Med. Dec. 28, 2011;19:74(1-12). doi: 10.1186/1757-7241-19-74.
Otero et al., Early goal-directed therapy in severe sepsis and septic shock revisited: Concepts, controversies, and contemporary findings. Chest. Nov. 2006;130(5):1579-95.
Yealy et al., A randomized trial of protocol-based care for early septic shock. N Engl J Med. May 1, 2014;370(18):1683-93. 16 pages. doi: 10.1056/NEJMoa1401602. Epub Mar. 18, 2014.
International Search Report and Written Opinion dated Nov. 16, 2016 for Application No. PCT/US2016/046915.
Berger et al., Shock index and early recognition of sepsis in the emergency department: Pilot study. Western J Emerg Med. Mar. 2013 ;14(2):168-74.
Chen et al., Decision tool for the early diagnosis of trauma patient hypovolemia. J Biomed Informatics. Jun. 2008;41(3):469-78. Epub Jan. 18, 2008.
Allgower et al., Schockindex. Deutsche Medizinische Wochenschrift. Oct. 1967;92(43):1947-50, with 2pg English translation of German Abstract, accessed online at https://www.thieme-connect.de/products/ejournals/ejournals/abstract/10.1055/x-0028--1106070?update=true. Published Apr. 16, 2009. Thieme E-Journals-DMW-German Medical Weekly Journal/Abstract.
Angus et al., Epidemiology of severe sepsis in the United States: Analysis of incidence, outcome, and associated costs of care. Crit Care Med. Jul. 2001;29(7):1303-10.
Barfod et al., Peripheral venous lactate at admission is associated with in-hospital mortality, a prospective cohort study. Acta Anaesthesiol Scand. Apr. 2015;59(4):514-23. doi: 10.1111/aas.12503.
Freund et al., Experiments with a new boosting algorithm. ICML. Machine Learning:Proc $13^{th}$ Intl Conf. 1996;96:148-56. 9 pages.
Frohlich et al., Predictors of outcome in decompensated liver disease: Validation of the SOFA-L score. Ir Med J. Apr. 2015;108(4):114-6. Accessed online Jun. 5, 2018 at http://archive.imj.ie//DesktopModules/IMJ/LookUps/PrintArticle.aspx?ArticleID=13991. 4 pages.
Howell et al., Occult hypoperfusion and mortality in patients with suspected infection. Intensive Care Med. Nov. 2007;33(11):1892-9. Epub Jul. 6, 2007.
Juneja et al., Admission hyperlactatemia: Causes, incidence, and impact on outcome of patients admitted in a general medical intensive care unit. J Crit Care. Jun. 2011;26(3):316-20. doi: 10.1016/j.jcrc.2010.11.009. Epub Jan. 20, 2011.
Liu et al., Hospital deaths in patients with sepsis from 2 independent cohorts. JAMA. Jul. 2, 2014;312(1):90-2.
Lovett et al., The vexatious vital: Neither clinical measurements by nurses nor an electronic monitor provides accurate measurements of respiratory rate in triage. Ann Emerg Med. Jan. 2005;45(1):68-76.
McLean et al., Investigating sepsis with biomarkers. BMJ. Feb. 7, 2015;350:h254. pp. 31-34. doi: 10.1136/bmj.h254.
Mikkelsen et al., Serum lactate is associated with mortality in severe sepsis independent of organ failure and shock. Crit Care Med. May 2009;37(5):1670-7. 8 pages. doi: 10.1097/CCM.0b013e31819fcf68. 8 pages.
Motulsky et al., Fitting models to biological data using linear and nonlinear regression: A practical guide to curve fitting. Oxford University Press. 2003. pp. 90.
Nguyen et al., Early lactate clearance is associated with improved outcome in severe sepsis and septic shock. Crit Care Med. Aug. 2004;32(8):1637-42.
Puskarich et al., Prognosis of emergency department patients with suspected infection and intermediate lactate levels: A systematic review. J Crit Care. Jun. 2014;29(3):334-9. doi: 10.1016/j.jcrc.2013.12.017. Epub Jan. 4, 2014.
Saeed et al., Multiparameter Intelligent Monitoring in Intensive Care II (MIMIC-II): A public-access intensive care unit database. Crit Care Med. May 2011;39(5):952-60. doi: 10.1097/CCM.0b013e31820a92c6. 18 pages.
Shapiro et al., Serum lactate as a predictor of mortality in emergency department patients with infection. Ann Emerg Med. May 2005;45(5):524-8.
Sprung et al., An evaluation of systemic inflammatory response syndrome signs in the Sepsis Occurrence in Acutely Ill Patients (SOAP) study. Intensive Care Med. Mar. 2006;32(3):421-7. Epub Feb. 15, 2006.
Suistomaa et al., Time-pattern of lactate and lactate to pyruvate ratio in the first 24 hours of intensive care emergency admissions. Shock. Jul. 2000;14(1):8-12.

(56) References Cited

OTHER PUBLICATIONS

Trzeciak et al. Serum lactate as a predictor of mortality in patients with infection. Intensive Care Med. Jun. 2007;33(6):970-7. Epub Mar. 13, 2007.
Vandromme et al., Lactate is a better predictor than systolic blood pressure for determining blood requirement and mortality: Could prehospital measures improve trauma triage? J Am Coll Surg. May 2010;210(5):861-7. doi: 10.1016/j.jamcollsurg.2010.01.012.
Wayman, Technical testing and evaluation of biometric identification devices. Ch. 17 in Biometrics, Personal Identification in Networked Society. 1996. Ed by Jain et al., Springer: New York. pp. 345-368.

* cited by examiner

SYSTEM AND METHODS TO PREDICT
SERUM LACTATE LEVEL

CROSS REFERENCE RELATED APPLICATIONS

This application claims the benefit under 35 U.S.C. § 119(e) of U.S. Provisional Application No. 62/204,292, filed Aug. 12, 2015, entitled "SYSTEM AND METHODS TO PREDICT SERUM LACTATE LEVEL," which is incorporated by reference herein in its entirety.

BACKGROUND

Serum lactate is an important biomarker for hypoperfusion and is useful in patient monitoring from critical care medicine to perioperative management. Serum lactate has, for instance, been shown to be an independent predictor of mortality in sepsis patients and an independent predictor of major complications after cardiac surgery; it is capable of stratifying patients by risk for developing shock; and serum lactate level also serves as a useful target for quantitative resuscitation. Current methods and systems for estimating serum lactate require a blood draw and laboratory test, which incur cost and delay.

SUMMARY

System and methods are disclosed herein for predicting a patient's serum lactate level. According to once aspect, arterial blood pressure and heart rate are measured from the patient and estimates of one or more cardiovascular parameters are computed from the measured arterial blood pressure and heart rate. One or more classifiers are provided that have been trained on a training data set including a reference set of arterial blood pressure, heart rate, and serum lactate levels. The one or more classifiers are used to estimate the serum lactate level of the patient.

Another aspect relates to a system including means for assigning a risk of sepsis to the patient depending on the estimated serum lactate level. The system further comprises means for estimating at least one of a total peripheral resistance, cardiac output and stroke volume of a patient using the measured arterial blood pressure and heart rate. In some implementations, the system further comprises means for including at least one of total peripheral resistance, cardiac output and stroke volume in the training data set. Another aspect relates to the system including means for extracting static parameters from history associated with the patient and incorporating in training the one or more classifiers, and wherein patient history includes demographic information and one or more lab values. In some embodiments, the system further comprises grouping patients with similar history in the training data. Another aspect of the invention relates a system including means for determining arterial blood pressure and heart rate from real-time wave forms. Another aspect of the system relates to a system comprising means for generating an alarm if the serum lactate level of the patient crosses a predetermined threshold.

In some embodiments, the system further comprises means for selecting a classifier from the one or more classifiers to estimate serum lactate level for a patient, wherein the selected classifier is based on a set of features including a median systolic blood pressure and a log-ratio that compares a first median heart rate for a length of time as measured at a beginning of a measurement and a second median heart rate for the length of time as measured at an end of the measurement and wherein the selected classifier has a highest median area under the curve value and a highest equal error rate value in comparison to other classifiers in the one or more classifiers.

In some implementations, a serum lactate is estimated for a patient. According to once aspect, arterial blood pressure and heart rate are measured from the patient. Estimates of one or more cardiovascular parameters are computed from the measured arterial blood pressure and heart rate. One or more classifiers are provided that have been trained on a training data set including a reference set of arterial blood pressure, heart rate, and serum lactate levels. The one or more classifiers are used to estimate the serum lactate level of the patient.

DETAILED DESCRIPTION

Serum lactate is an important marker of risk for adverse outcomes (such as mortality and organ failure, for example) in critically ill patients. Lactate is produced and consumed throughout the body. However, lactate production increases in hypoxic conditions, when the cells of the body are deprived of oxygen.

Hemodynamic disruptions (including those resulting from trauma, cardiac arrest, and sepsis, for example) may also affect lactate production. Hemodynamic disruptions lead to increased lactate production, which registers in blood draws. For this reason, lactate is regarded as an important bio-marker for risk in patients. However, lactate may also be elevated due to cancer, strenuous exercise, metabolic problems, alcohol intoxication, and medication use. Knowledge of the patient and the causes of hyperlactatemia are essential to providing appropriate care.

Therefore, serum lactate is an important risk-stratification tool for critically ill patients with complaints of infectious or non-infectious origin. The known methods of determining serum lactate level include sending an arterial or venous blood draw to a laboratory blood gas analyzer and point-of-care devices that use capillary blood from a finger prick, among others. These approaches incur cost and delay. The system and methods disclosed herein describe how to estimate or predict the serum lactate level of a patient in real time and over a time interval.

For the purposes of this application, a serum lactate level may refer to a determined quantity of serum lactate in a patient, or a serum lactate category, where the categorization of the serum lactate level is based on a predetermined criteria. Similarly, for the purposes of this application, heart rate may be a measured heart rate of a patient or an estimated heart rate of the patient, and arterial blood pressure may be a measured arterial blood pressure of a patient or an estimated blood pressure of a patient.

Figure 1:
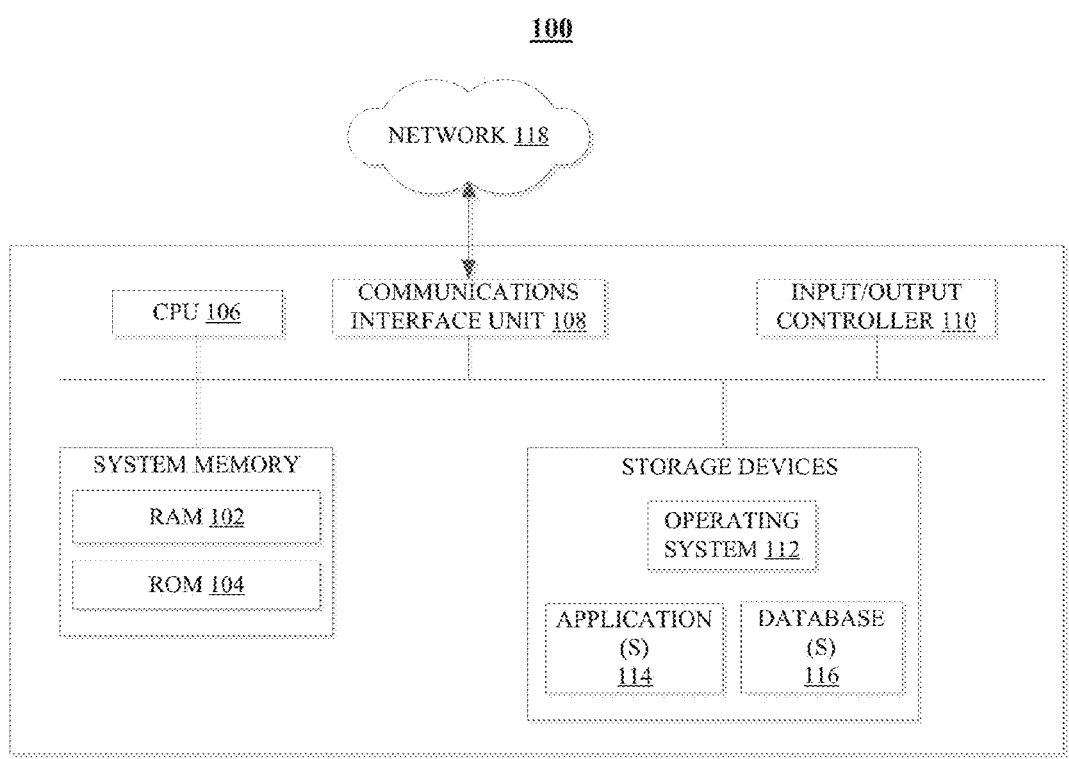
FIG. 1 is block diagram of a computing device for performing any of the processes described herein, according to an illustrative embodiment.

FIG. 1 is a block diagram of a computing device for performing any of the processes described herein, according to an illustrative embodiment. Each of the components of these systems may be implemented on one or more computing devices 100. In certain aspects, a plurality of the components of these systems may be included within one computing device 100. In certain implementations, a component and a storage device may be implemented across several computing devices 100.

The computing device 100 comprises at least one communications interface unit, an input/output controller 110, system memory, and one or more data storage devices. The system memory includes at least one random access memory (RAM 102) and at least one read-only memory (ROM 104). All of these elements are in communication with a central processing unit (CPU 106) to facilitate the operation of the computing device 600. The computing device 600 may be configured in many different ways. For example, the computing device 600 may be a conventional standalone computer or, alternatively, the functions of computing device 600 may be distributed across multiple computer systems and architectures. In FIG. 1, the computing device 100 is linked, via network or local network, to other servers or systems.

The computing device 100 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 108 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 106 comprises a processor, such as one or more conventional microprocessors and one or more supplementary co-processors such as math co-processors for offloading workload from the CPU 806. The CPU 106 is in communication with the communications interface unit 108 and the input/output controller 110, through which the CPU 106 communicates with other devices such as other servers, user terminals, or devices. The communications interface unit 108 and the input/output controller 110 may include multiple communication channels for simultaneous communication with, for example, other processors, servers or client terminals in the network 118.

The CPU 106 is also in communication with the data storage device. The data storage device may comprise an appropriate combination of magnetic, optical or semiconductor memory, and may include, for example, RAM 102, ROM 104, flash drive, an optical disc such as a compact disc or a hard disk or drive. The CPU 106 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 106 may be connected to the data storage device via the communications interface unit 108. The CPU 106 may be configured to perform one or more particular processing functions.

The data storage device may store, for example, (i) an operating system 112 for the computing device 100; (ii) one or more applications 114 (e.g., computer program code or a computer program product) adapted to direct the CPU 106 in accordance with the systems and methods described here, and particularly in accordance with the processes described in detail with regard to the CPU 106; or (iii) database(s) 116 adapted to store information that may be utilized to store information required by the program.

The operating system 112 and applications 114 may be stored, for example, in a compressed, an uncompiled and an encrypted format, and may include computer program code. The instructions of the program may be read into a main memory of the processor from a computer-readable medium other than the data storage device, such as from the ROM 104 or from the RAM 102. While execution of sequences of instructions in the program causes the CPU 106 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions in relation to performing classification of serum lactate levels based on heart rate and serum lactate levels as described herein. The program also may include program elements such as an operating system 112, a database management system and "device drivers" that allow the processor to interface with computer peripheral devices (e.g., a video display, a keyboard, a computer mouse, etc.) via the input/output controller 110.

The term "computer-readable medium" as used herein refers to any non-transitory medium that provides or participates in providing instructions to the processor of the computing device 100 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 106 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 100 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Figure 2:
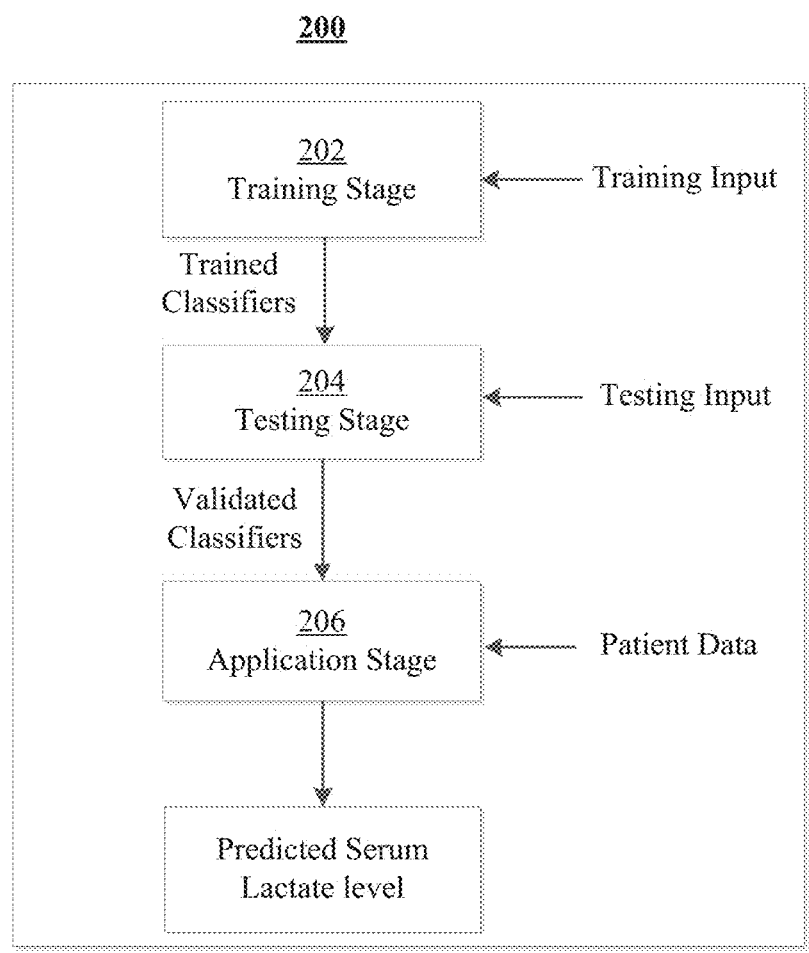
FIG. 2 is a block diagram of a classification system for determining a serum lactate level associated with heart rate and arterial blood pressure, according to an illustrative embodiment.

FIG. 2 is an illustrative block diagram of a classification system 200 for determining a serum lactate level associated with a patient. The system 200 includes a training stage 202, a testing stage 204 and an application stage 206. Inputs to the system 200 include training input data to train a set of classifiers, testing input data to test the set of trained classifiers and data recorded from a patient. The system 200 uses the trained and tested classifiers and the patient data to provide an estimate or predicted serum lactate level of the patient. In some embodiments, the set of classifiers may only comprise a single classifier.

The training stage 202 receives a set of training input data and provides a set of trained classifiers to the testing stage 204. The set of training input data includes a set of training heart rate and arterial blood pressure data recorded from a first group of patients and a set of the patients' serum lactate levels. In some embodiments, the set of training input data may contain gaps in some segments. For example, for some patients in the training data, the demographic information may be incomplete or may be implausible (an 800 year old man, for example). In that case, the training input data may also include synthetic data. The synthetic data may be generated by users or testers associated with the process for the purposes of covering correlations between heart rate and arterial blood pressure and serum lactate levels that are not covered in data from the first group of patients. In some embodiments, the training data may include solely synthetic data if the users associated with the training stage may wish to train the classifiers on a very specific set of characteristics and correlations that are not available in historic data of the first group of patients. For example, the user associated with the training stage may be a clinician (such as a doctor or a nurse) or a researcher at a hospital. In the process of importing the training input data, the user may identify gaps in the training data and might want to add some synthetic training data to fill these gaps. The gaps may include certain values or ranges of heart rate and arterial blood pressure that are not part of the training data. In some embodiments, these gaps in training data may not be part of the predictions of serum lactate levels made for patients. In some embodiments, the users associated with the training stage may be developers who add synthetic training data to fill in gaps in the training data to examine the performance of the training stage under different conditions. In some embodiments, certain algorithms used to generate classifiers (for example generative adversarial neural nets), involve the learning of a generative model to produce examples that would trick the classifier. In such cases, synthetic data is generated to cover rare cases that may trick the classifier. In some embodiments, the signals received from the training data are noisy, and potentially disrupted. In such cases the estimated heart rate and arterial blood pressure values used to replace the noisy signals may be synthetic based on informed models of noise processes, channel characteristics and the physiological condition of the patient. For example, the relation of heart rate to pulse, cardiac output and pulse pressure may influence the synthetic estimation of noisy heart rate values. The training data may include windowed averages of heart rate extracted from electrocardiogram (ECG) signals and second by second moving averages of arterial blood pressure obtained through a catheter. In some embodiments, the heart rate and arterial blood pressure data may be partitioned using different time windows. For example, the heart rate may be averaged over multiple seconds or minutes 5 seconds, 10 seconds, 60 seconds, and 5 minutes and so on. Similarly, the arterial blood pressure may be averaged over multiple seconds or minutes like 5 seconds, 10 seconds, and 60 seconds and so on. The time window of averaging these parameters may be manually specified by a user associated with the training input data. In some embodiments, it may be preferable to create longer partition of time windows of the training data because it takes time for imbalances in oxygen delivery and demand to reflect in serum lactate levels. The set of training input data may also include parameters that may not be monitored regularly (such as the patient's medical history and demographic information, for example). In some embodiments, patients with similar history or demographic information are grouped together. This is done to provide classifiers to predict serum lactate levels for a particular condition. For example, all patients who have been recuperating post cardiac arrests are grouped together in one training data set, and all patients below the age of 50 are grouped together in a different training data set. The evolution of patients' serum lactate levels over the next few hours is very predictive of outcome. The risk of sepsis for these groups will be influenced by their preexisting conditions. Therefore classifiers are trained on specific groups to yield better results in predicting serum lactate level for a wide range of patients. In some embodiments, patients may be grouped by trauma experienced, experience of sepsis-like responses or perioperative patients. There are likely clues about perfusion adequacy and in the heart rate and arterial blood pressure of all such patients. The training stage 202 may select subsets of training input data and train a classifier on each selected subset. The components of the training stage 202 are described in detail in relation to FIG. 3, and the training stage 202 may operate on the training input data according to the method as described in FIG. 6.

The testing stage 204 receives the set of trained classifiers from the training stage 202 and a set of testing input data. The set of testing input data includes a set of testing heart rate and arterial blood pressure recorded from a second group of patients and a set of the patients' serum lactate levels. The components of the testing stage 204 are described in detail in relation to FIG. 4, and the testing stage may operate on the testing input data and the trained classifiers according to the method described in relation to FIG. 7. In particular, the testing stage 204 may aggregate votes from the trained classifiers operating on the testing input data and compare the serum lactate levels predicted by the aggregated votes to the corresponding set of actual serum lactate levels from the second group of patients in the testing input data. If there is a sufficient match between the predicted and actual serum lactate levels, the testing stage 204 validates the classifiers and provides the validated classifiers to the application stage 206.

The application stage 206 receives the set of validated classifiers from the testing stage 204 and data recorded from a patient. The data may include a heart rate, arterial blood pressure and parameters not monitored regularly, (such as the patient's medical history and demographic information, for example) and the serum lactate level of the patient may be unknown. The components of the application stage 206 are described in detail in relation to FIG. 5, and the application stage 206 may operate on the patient data and the validated classifiers according to the method described in FIG. 8. In particular, the application stage 206 may aggregate votes from the validated classifiers operating on the patient data to determine a predicted serum lactate level associated with the patient. The predicted serum lactate level may be provided by the system 200 to a user such as a medical professional.

Figure 3:
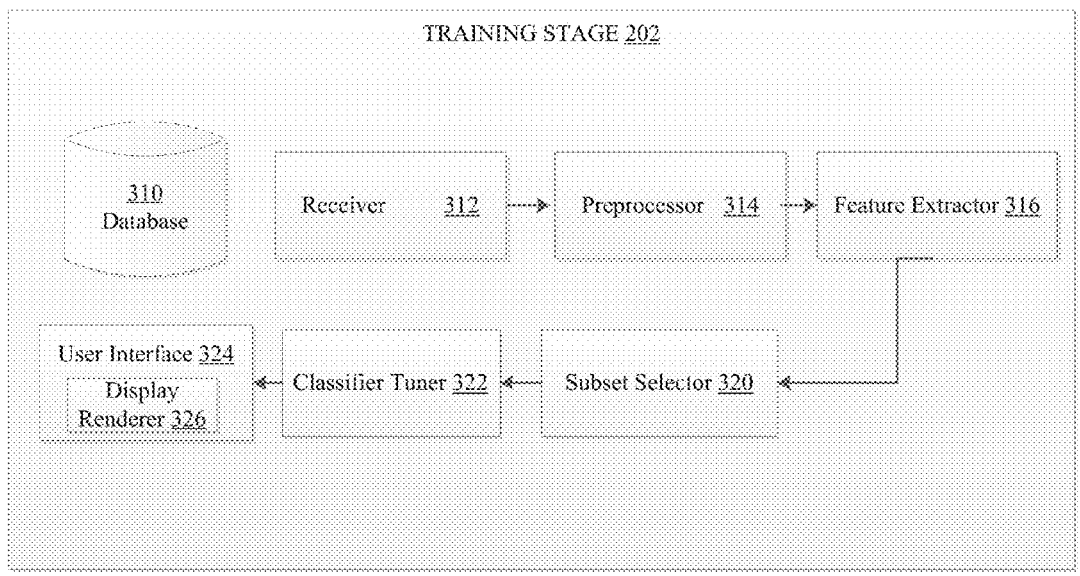
FIG. 3 is a block diagram of a training system for training a set of classifiers on heart rate and arterial blood pressure, according to an illustrative embodiment.

FIG. 3 is an illustrative block diagram 300 of a training stage 202 for training a set of classifiers on a set of training heart rate and arterial blood pressure. The training stage 202 includes a database 310, a receiver 312, a preprocessor 314, a feature extractor 316, a subset selector 320, a classifier tuner 322, and a user interface 324 that includes a display renderer 326. The training stage 202 may operate on training input data according to the method described in relation to FIG. 6. The database 310 may also be used to store any data related to training a set of classifiers as described herein.

The training stage 202 receives training input data over the receiver 312. The receiver 312 may provide an interface with a data source, which may transmit heart rate and arterial blood pressure and corresponding patient serum lactate level to the training stage 202. The training input data includes second-by-second windowed averages of heart rate extracted from electrocardiogram (ECG) signals as well as second by second of moving averages of arterial blood pressure measured through a catheter along with corresponding serum lactate levels are for each of those values. In some embodiments, the database may include a record of intervention by a clinician at a certain point in a patient's treatment. In such cases, the database may include a track of interventions made and corresponding serum lactate level to predict an intervention by a clinician based on historical patient data and clinical guidelines.

After the training data is received by the receiver 312, the preprocessor prepares the training data that may be used to train the classifiers. The preprocessing may involve partitioning the data into various sets and removing outlier values. As discussed in the training stage 202, the data may be partitioned using different time windows. For example, the heart rate may be averaged over multiple seconds and minutes, like 5 seconds, 10 seconds, 60, and 5 minutes seconds and so on. Similarly, the arterial blood pressure may be averaged over multiple seconds or minutes like 5 seconds, 10 seconds, and 60 seconds and so on. In some embodiments, the preprocessor may also include filtering out those records for which some parameters are not available. One example of the steps involved in preprocessing is described in relation to FIG. 13.

After the training data is preprocessed by the preprocessor 314, the feature extractor 316 extracts features from the remaining preprocessed heart rate and blood pressure values. The features may be characteristics of the heart rate and arterial blood pressure that are directly correlated to serum lactate levels. Features may be indicative of shock index, total peripheral resistance, stroke volume, cardiac output or any other suitable feature of a patient. Details regarding the determination of total peripheral resistance are described in U.S. Pat. No. 8,282,564 filed May 15, 2008, the contents of which are hereby incorporated herein by reference in their entirety. Use of feature extraction is advantageous because features express discriminative information in a compact form that is better suited for use by the machine learning algorithm and for the establishment of a link to serum lactate level than the preprocessed data. In addition, these features are straightforward to extract from the heart rate and arterial blood pressure. In addition to features extracted from heart rate and arterial blood pressure, other features (such as patient history, demographic information, lab values, interventions nurse verified number of vitals and other parameters that may not be continuously monitored, for example) may also be extracted from the patient record. In some embodiments, the derived parameters of total peripheral resistance, shock index and cardiac output may be used to predict mortality and other adverse events better than their constituent heart rate and arterial blood pressure alone. These adverse events may be associated with the serum lactate level to stratify patient risk of sepsis as discussed with respect to FIG. 8. These features tune the classifier to estimate serum lactate levels in the training stage.

After the feature extractor 316 extracts the features from the training set of heart rate and arterial blood pressure, the subset selector 320 selects subsets of the training data. As an example, the subset selector 320 may randomly select a fixed number of the patients in the first group of patients to form a subset of the training data. The number of selected patients may be based on user input received over the user interface 324. For example, the user input may include the number of patients to select, or the user input may include a percentage of the number of patients to select. Additional subsets may also be subsequently selected in the same way. The number of selected subsets may be based on a number of desired classifiers, and may be determined based on user input received over the user interface 324. The total number of selected subsets may be referred to herein as N.

After N subsets of the training heart rate and arterial blood pressure are selected, the classifier tuner 322 trains a classifier on each subset to determine a decision rule for the subset. In particular, the decision rule may be based on the extracted features from the training data set and the known serum lactate levels of the patients in the training data set. A classifier may provide a map from any set to feature values to a serum lactate level. In some embodiments, the classifier may provide a map from a set of a heart rate and corresponding arterial blood pressure value to a serum lactate level of a patient. Thus, a total of N classifiers are generated from the N subsets of the training heart rate and arterial and blood pressure.

The output of the training stage 202 is a set of N classifiers that have been trained on N different subsets of the first portion of the training input data to map the heart rate and arterial blood pressure to a serum lactate level.

Figure 4:
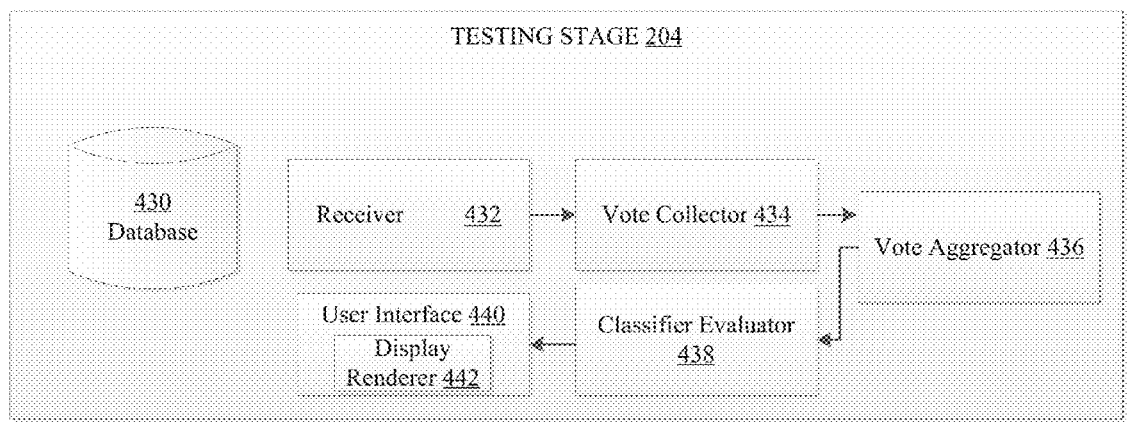
FIG. 4 is a block diagram of a testing system for testing a set of trained classifiers on heart rate and arterial blood pressure, according to an illustrative embodiment.

FIG. 4 is an illustrative block diagram 400 of a testing stage 204 for testing a set of classifiers on a set of testing heart rate and arterial blood pressure. The testing stage of 204 includes several components for executing the process described herein. In particular, the testing stage 204 includes a database 430, a receiver 432, a vote collector 434, a vote aggregator 436, a classifier evaluator 438, and a user interface 440 including a display renderer 442. The testing stage 204 may operate on testing input data and a set of trained classifiers according to the method described in relation to FIG. 7. The database 430 may be used to store any data related to testing a set of classifiers as described herein.

The testing stage 204 receives testing input data and a set of N trained classifiers over the receiver 432. The receiver 432 may provide an interface with a data source, which may transmit testing heart rate and arterial blood pressure and corresponding serum lactate levels to the testing stage 204. The testing heart rate and arterial blood pressure may be recorded from a second group of patients (i.e., which may be different from the first group of patients making up the set of training data used in the training stage 202), and the serum lactate levels of the second group of patients may be known and transmitted to the receiver 432. In particular, there may be K patients in the second group of patients, such that the testing heart rate and arterial blood pressure include K different sets of values. The receiver 432 may also form an interface with the training stage 202 to receive a set of trained classifiers from the training stage 202. In particular, each trained classifier in the set of trained classifiers may include a decision rule based on patients' heart rate and arterial blood pressure data indicating a most likely serum lactate level corresponding to the patient.

After the testing data and the set of classifiers are received, the vote collector 434 collects votes from the N trained classifiers based on the heart rate and arterial blood pressure record from each patient in the second group of patients. The votes correspond to candidate serum lactate levels that are selected based on the decision rule of each trained classifier. The time series data received by the testing stage for each patient in the second group of patient has heart rate data derived from the patient's ECG and arterial blood pressure measured from an arterial catheter. The testing stage then proceeds to divide this time series data into smaller time windows to be processed. As described in relation to the training stage 202, the data for the testing stage may be divided by time intervals of 5 seconds, 10 seconds, 60 seconds, 5 minutes or any other suitable time interval. Each time window of the ECG data may be representative of a number of heart beats. The heart rate for each time window is averaged over the heart beats present in the time window Similarly, the arterial blood pressure is averaged over the time window. In particular, a number J windows of heart rate data and arterial blood pressure values may be selected (J may be determined based on user input received over the user interface 440, for example), and for each patient, the classifiers may vote on each of the J windows of heart rate data and arterial blood pressure values. Thus, for each patient record in the set of testing data, the vote collector 434 determines N×J votes for the candidate serum lactate levels.

After the votes have been collected, the vote aggregator 436 aggregates the votes. In certain implementations, the vote aggregator 436 combines the votes in two steps for each patient. A first step includes a "heart rate window" aggregation, and a second step includes a "per patient" aggregation. The result of the two steps is a determination of a most likely serum lactate level of a patient in the second group of patients.

In a first step, the vote aggregator 436 performs a "per heart rate window" aggregation by combining the N votes across the N classifiers (i.e., one vote per classifier) for a given heart rate window. For example, the vote aggregator 436 may determine a most likely candidate serum lactate level corresponding to a heart rate window by determining whether the number of votes for the serum lactate level satisfy some criterion. For example, a threshold value may be based on user input received over the user interface 440 and may be a fixed number or a fixed percentage of the N votes. In another example, the criterion may require the vote aggregator 436 to simply select the candidate serum lactate level with the most votes, regardless of whether the number of votes exceeds some threshold. In another example, the N votes may be combined to obtain an average ranging from 0 to 1 that is retained in the next voting step. The vote aggregator 436 repeats this for each of the J heart rate windows and arterial blood pressure in a patient's record to provide a set of J resulting votes (i.e., one resulting vote per heart rate window).

In a second step, the vote aggregator 436 performs a "per patient" aggregation by combining the set of J resulting votes to determine a most likely serum lactate level for the patient. For example, the vote aggregator 436 may determine a most likely serum lactate level of the patient by determining a probability of the serum lactate level of a patient based on the votes received for different values. For example, a threshold value may be based on user input received over the user interface 440 and may be a fixed number or a fixed percentage of the J resulting votes. In another example, the criterion may require the vote aggregator 436 to simply select the candidate serum lactate level with the most votes, regardless of whether the number of votes exceeds some threshold. If there are K patients in the second group of patients, the vote aggregator 436 repeats this for each of the K patients to provide a set of K predicted serum lactate levels (i.e., one serum lactate level per patient).

After the votes are aggregated, the classifier evaluator 438 plots a receiver operating characteristic (ROC) curve to obtain a range of expected performance of the classifier on the testing data. In some embodiments, the ROC's derived from the training stage are plotted to generate a good error bar to predict obtain a range of expected performance of the classifier. This process is repeated for each classifier generated in the training stage 202 (see FIG. 9). In some embodiments, if the testing stage employs a regression based method to on the testing data, the evaluation may use different criteria, lime mean squared error, for example.

The classifier evaluator 438 evaluates each classifier based on the statistics gathered over the training of the classifiers. In some embodiments, the statistics used to evaluate the classifiers are Area Under the Curve (AUC) and Equal Error Rate (EER) values (see FIG. 10). Based on the information gathered from the receiver operating curve and the AUC and EER values, and a predetermined algorithm, the classifier evaluator 438 selects the most suitable classifier from the set of classifier that were received from the training stage 202. In some embodiments, the best classifier has one of the highest AUC and EER values. However, the difference between the classifiers corresponding to the highest AUC and EER values is not particularly relevant.

At the end of the testing stage 204, a subset of the N classifiers from the training stage 202 are selected. The selection of these classifiers is based on their performance over the testing data set. In some embodiments, the classifiers are selected based on the accuracy of the predicted serum lactate levels.

The testing stage depicted in FIG. 4 is one out of many different ways to implement a testing stage to test classifiers and data received from the training stage 202. In some embodiments, a bagging voting scheme was used to reduce variance and bias in generation of the predictive model for predicting the serum lactate level in a patient. In the bagging voting scheme, an ensemble classifier is generated from a fixed number of constituent classifiers, where each classifier is trained on a different subset of the data set. To evaluate the classifier type, the classifier votes on the testing data. In some embodiments, a training data set may be partitioned into an 80% training set and 20% testing set a 100 times, to generate error bars on ROC curves generated for each classifier for each partition. From each 80% training set, D samples may be created by sampling with replacement (For example D may be 25 or 50 and so on as defined by the user, depending on the experiment). All windows or records in the 80% set may be sampled, but because the sampling is with replacement, these samples are expected to span over about 70% of the training set). The same classifier may be then trained on each of these D cuts. These D trained classifiers then vote on each record in the 20% testing set. The classifier may be evaluated based on the ensemble performance on the 20% test set.

In some embodiments, boosted-decision tree classifiers were used to test the training data to generate a predictive model to predict serum lactate level in a patient. In boosted decision trees, the classifiers were varied based on tuning features, for example the allowed depth of the constituent decision trees. Examples of features included in the classifiers are median heart rate over the data window, median shock index over the hour before the lactate reading, ratio of total peripheral resistance in the first two hours to that over the last two hours, and accumulated area of heart rate over 75 beats per minute. Each classifier (also known as constituent tree) in the boosted decision tree votes on a likelihood of serum lactate level values for each patient. The final decision of the serum lactate level for a patient is made by computing a weighted sum of all the constituent trees' predictions for serum lactate level. In some embodiments, the constituent classifiers are decision trees grown greedily on a data set DB. The data sets DB are the same size as the 80% training set but are sampled with replacement so are expected to contain repeated data points. The sampling with replacement is done not uniformly at random, as in the bagging voting scheme discussed above; rather, it is a weighted sampling that privileges those points in the 80% training cut that the decision trees previously grown misclassified, i.e., during training, one generally looks at performance on the training set.

Figure 5:
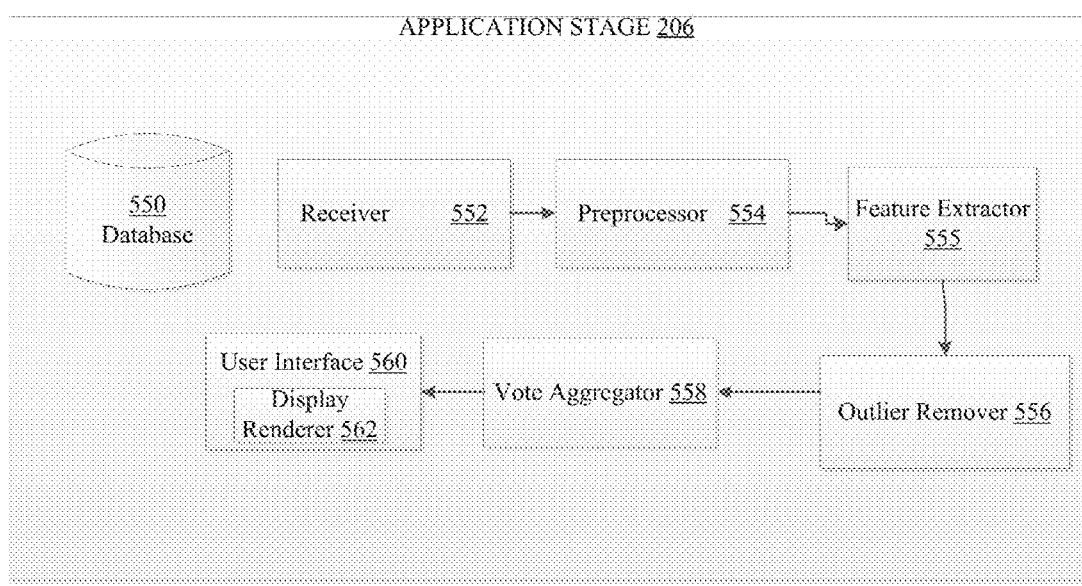
FIG. 5 is a block diagram of an application system for using trained and tested classifiers to determine a serum lactate level associated with heart rate and arterial blood pressure, according to an illustrative embodiment.

FIG. 5 is an illustrative block diagram of an application stage 206 for applying a set of validated classifiers to a patient's data to predict a serum lactate level of the patient. The application stage 206 includes several components for executing the processes described herein. In particular, the application stage 206 includes a database 550, a receiver 552, a preprocessor 554, a feature extractor 555, an outlier remover 556, a vote aggregator 558, and a user interface 560 including a display renderer 562. The application stage 206 may operate on a patient's data and a set of validated classifiers according to the method as described in relation to FIG. 8. The database 550 may be used to store any data related to applying a set of classifiers to a patient's data as described herein.

The application stage 206 receives a patient's data and a set of validated classifiers over the receiver 552. The receiver 552 may provide an interface with a data source, which may transmit the patient's heart rate and arterial blood pressure data to the application stage 206. The patient's heart rate and arterial blood pressure may be recorded from a patient not included in either the first or second group of patients, and the serum lactate level of the patient may be unknown. In particular, the patient's heart rate and arterial blood pressure data may include a heart rate window composed of a number of heart beats. The receiver 552 may also form an interface with the testing stage 204 to receive a set of validated classifiers from the testing stage 204. In particular, each validated classifier in the set of validated classifiers may include a decision rule based on one or several patients' heart rate and arterial blood pressure vales data indicating a most likely serum lactate level corresponding to the patient.

After the patient's data and the set of validated classifiers are received, the preprocessor 554 may process the patient's data to convert the data into a suitable form for performing analysis. For example, the preprocessor 554 may generate a template view of the patient's heart rate and arterial blood pressure data by identifying a suitable time period to partition the heart rate data to generate meaningful heart windows. In some embodiments, the heart rate and arterial blood pressure of the patient may be averaged over time before the serum lactate level is calculated.

The feature extractor 555 extracts features from the heart rate windows and arterial blood pressure. The features may be characteristics of the heart rate window and arterial blood pressure that are directly correlated to serum lactate levels. Features may be indicative of heart health, and examples of features include stroke volume, total peripheral resistance, cardiac output, shock index or any other suitable feature of a heart.

In certain implementations, the range of serum lactate levels are specified before dividing the data into different categories. In particular, the outlier remover 556 may be configured to identify and remove outlier serum lactate levels. For example, serum lactate levels that precede a low lactate reading but are drawn from a patient of high lactate reading may be excluded from analysis and classification.

After outlier serum lactate levels are removed, the validated classifiers are applied to the patient's heart rate and arterial blood pressure data, and the vote aggregator 558 collects and combines the votes selected by each validated classifier in a similar manner as the vote aggregator 436 of the testing stage 204. As described in relation to FIG. 4, the vote aggregator 558 may aggregate the votes in two steps. A first step may include a "per heart rate window" aggregation, and a second step may include a "per patient" aggregation.

The result of the two steps is a selection of a most likely serum lactate level of the patient.

The systems shown in FIGS. 2-5 may provide a serum lactate level as described with reference to flowcharts in FIGS. 6-8. In particular, the training stage 202 may use the method shown in FIG. 6 to train a set of classifiers on a set of training heart rate and arterial blood pressure data. After the set of classifiers are trained, the testing stage may use the method shown in FIG. 7 to validate the set of trained classifiers. Finally, the application stage may use the method shown in FIG. 8 to apply the validated classifiers to a patient's heart rate and arterial blood pressure data to identify a predicted serum lactate level of the patient.

Figure 6:
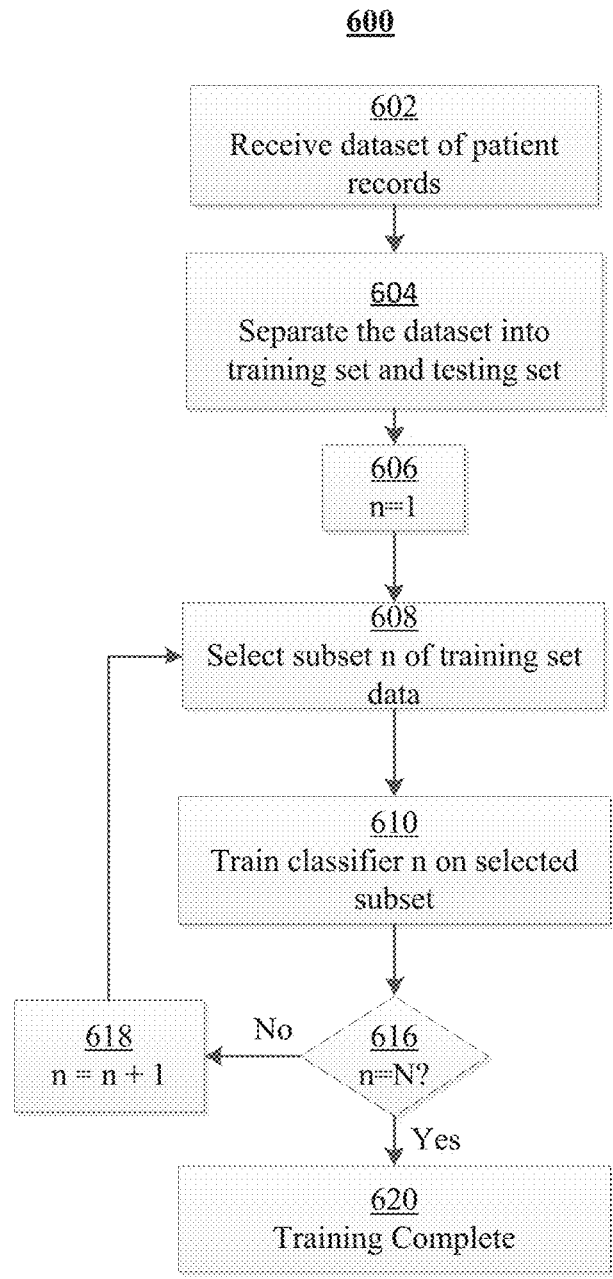
FIG. 6 is a flow diagram depicting a process, at the training stage, for training a set of classifiers on heart rate and arterial blood pressure, according to an illustrative embodiment.

FIG. 6 is a flowchart of a method used by the training stage 202 to train a set of classifiers on a set of training data. Classifiers are trained on a training set of heart rate and arterial blood pressure data and their corresponding features. In particular, the training set of heart rate and arterial blood pressure data includes a set of heart rate and arterial blood pressure data from patients with corresponding known serum lactate levels. In certain implementations, the serum lactate levels are a biomarker for patient risk-stratification of sepsis. More generally, serum lactate levels may be caused by poor tissue perfusion due to sepsis caused hypertension or microcirculatory failure. Alternatively, a patient may be determined to have a serum lactate level within an acceptable range. Depending on a patient's serum lactate level, heart rate and arterial blood pressure associated with the patient may exhibit different features. To train a classifier, a subset of the training set is selected (a subset of the records or patients in the training set, for example), and a classifier is generated based on the features of the selected subset.

The method 600 includes the steps of receiving a dataset of heart rate and arterial blood pressure (step 602), separating the dataset into a training set and a testing set (step 604), and initializing one iteration parameter n to one (step 606). A subset n of the training set data is selected (step 608), and a classifier n is trained on the selected subset (step 610). Steps 608 and 610 are repeated until the desired numbers of classifiers (i.e., N) have been trained At step 602, a dataset of heart rate and arterial blood pressure is received, for which patient serum lactate levels are known. At step 604, the received dataset is separated into a training set and a testing set. The training set is used to develop the classifiers and is provided as input to the training stage 202. The testing set is used to assess the performance of the resulting classifiers and is provided as input to the testing stage 204. An example method of assessing the performance of the classifiers in the testing stage 204 is described in relation to FIG. 7.

At step 606, one iteration parameter n is initialized to one. The iteration parameter n is representative of a selected subset of the training set.

At step 608, the subset selector 320 selects an $n^{th}$ subset of the training set data. As an example, a random subset of the training set data may be selected. For example, if there are 100 patients in the training set data, heart rate and arterial blood pressure from 80 patients may be randomly selected to form the subset n. Optionally, the training set data may be processed by the preprocessor 314 (i.e., to get the training set data into a suitable form), the feature extractor 316 (i.e., to extract features from the heart rate and arterial blood pressure), and/or the outlier remover 318 in any order. These processes are described in more detail in relation to FIG. 3.

At step 610, the $n^{th}$ classifier is trained on the corresponding subset. To train a classifier, a number of heart rate windows of the patients in the $n^{th}$ subset may be used. This number may be defined by the user. Because the serum lactate level of the patients in the training set are known, the $n^{th}$ classifier is trained on the features of the patient heart rate windows and arterial blood pressure. In some embodiments, to train a classifier, the classifier tuner 322 may define a decision rule, for which a set of heart rate window and arterial blood pressure values may be mapped to a serum lactate level. The classifiers are trained on every heart rate window combined with a corresponding blood pressure value as present in the database.

At decision block 616, it is determined whether the iteration parameter n equals the desired total number of subsets N. If not, the iteration parameter n is incremented at step 618 and the process returns to step 608 to select another subset of training set data.

When iteration parameter n has reached its final value, training is complete at step 620. In particular, as a result of the training, N classifiers have been generated. The classifiers may be different because they were tuned for optimal performance on different subsets of the training set records, though they all had the same mathematical/computational structure.

Figure 7:
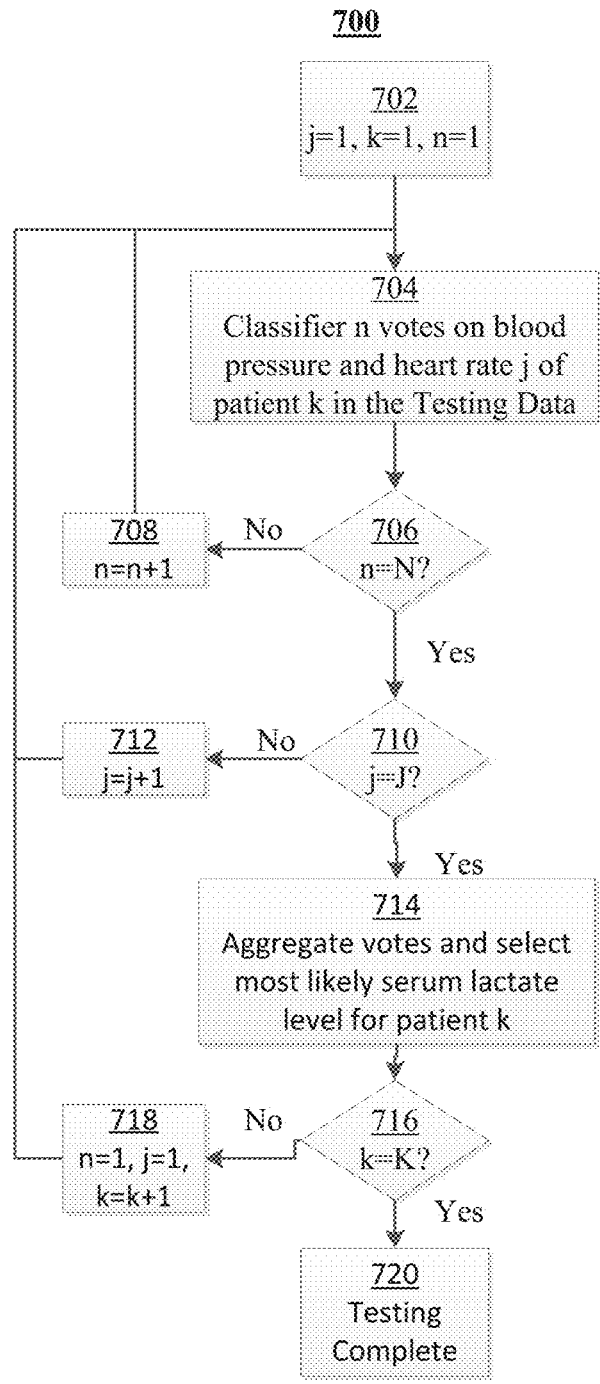
FIG. 7 is a flow diagram depicting a process, at the testing stage, for testing a set of trained classifiers on heart rate and arterial blood pressure, according to an illustrative embodiment.

FIG. 7 is a flowchart of a method used by the testing stage 204 to test a set of trained classifiers on a set of testing data. The method 700 includes the steps of initializing three iteration parameters j, k, and n to one (step 702), and allowing classifier n to vote on the heart rate window j of a patient k in the testing data. For each patient k, this process is repeated N (number of classifiers)×J (number of heart rate windows examined) times. When the voting process is complete for patient k, the votes are aggregated, and the probability of the serum lactate level for patient k is determined. The most probable serum lactate level is selected to the serum lactate level of the patient (step 714). This process is repeated for the patients in the testing database until the testing process is complete (step 720).

At step 702, three iteration parameters n, j, and k are each initialized to one. The iteration parameter n is representative of a classifier, the iteration parameter j is representative of a heart rate window, and the iteration parameter k is representative of a patient.

At step 704, the $n^{th}$ classifier votes on the $j^{th}$ heart rate window of the $k^{th}$ patient in the testing data set. For example, the decision rule of a classifier may indicate that a particular feature perfectly discriminates between two serum lactate levels. In this case, the classifier may use the same feature on the testing dataset to cast its vote. In general, the decision rule of the $n^{th}$ classifier is applied to one or more extracted features of the $j^{th}$ heart rate window of the $k^{th}$ patient.

At decision block 706, it is determined whether the iteration parameter n equals the desired total number of classifiers N. If not, the iteration parameter is incremented at step 708, and the process returns to step 704 for the next classifier to vote.

At decision block 710, it is determined whether the iteration parameter j equals the desired total number of respiratory cycles J to evaluate in a patient. If not, the iteration parameter j is incremented and the iteration parameter n is reinitialized to one at step 712, and the process returns to step 704 for the $1^{st}$ classifier to vote on the next heart rate window for the $k^{th}$ patient.

When both iteration parameter n and j reach their final values, the vote aggregator 436 aggregates the votes across the N classifiers and across the J heart rate windows to select the most likely serum lactate level for patient k at step 714. As an example, the vote aggregation may be performed in two stages. For example, each of the N classifiers has voted on each of the J heart rate windows, classifying each heart rate window to a serum lactate level, for example. In one embodiment, the votes across the N classifiers are aggregated for each heart rate window, resulting in J votes (one for each heart rate window). Then, the J votes may be aggregated. In an example, to aggregate votes, the majority (or some other fraction) of the votes may be selected. In an example, N=50 and J=35. Each classifier votes on each of the 35 first valid heart rate windows in the new test record, classifying each heart rate window to a serum lactate level. Whatever the majority (or some other selected fraction) of the verdicts comes out to be, out of the 35 votes, is the determination by that classifier of the serum lactate level of that record (as opposed to each individual heart rate window).

After the voting process for the first patient in the testing group has been completed, the iteration parameters n and j are both reinitialized to one, and the iteration parameter k is incremented at step 718. This voting process is repeated for the remaining patients until testing is complete at step 720, when the iteration parameter k reaches K at decision block 716.

Figure 8:
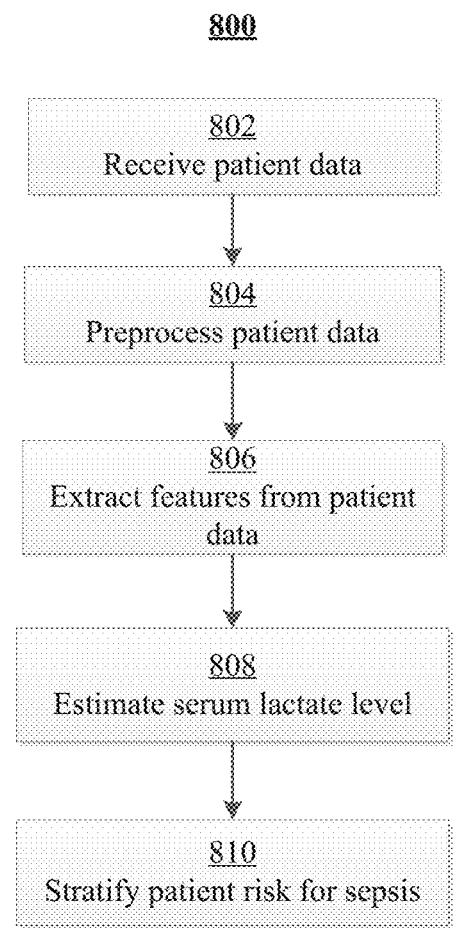
FIG. 8 is a flow diagram depicting a process, at the application stage, for using validated (trained and tested) classifiers to determine a serum lactate level associated with heart rate and arterial blood pressure, according to an illustrative embodiment.

FIG. 8 is a flowchart of a method used by the application stage 206 to apply validated classifiers (i.e. received from testing save 204) to a patient's heart rate and arterial blood pressure data to predict a serum lactate level of the patient. The method 800 includes the steps of receiving patient data (step 802), preprocessing patient data (step 804), and extracting features from the preprocessed data (step 806) to estimate a serum lactate level for a patient (808). The estimated serum lactate level is used to stratify risk of sepsis of a patient (step 810).

At step 802, a the receiver 552 receives a patient's data including heart rate and arterial blood pressure. In particular, the heart rate may be a set of second-by-second windowed averages extracted from electrocardiogram signals of a patient and the arterial blood pressure may be obtained through an arterial catheter installed in the patient.

At step 804, the preprocessor 554 processes the incoming stream of heart rate and arterial blood pressure data. As an example, the incoming stream of heart rate and arterial blood pressure may be grouped by number of heart rate windows.

At step 806, the feature extractor 555 extracts patient features from the incoming heart rate and arterial blood pressure data. This stage also includes feature extraction from patient record, for example patient history, demographic information and other static parameters associated with the patient.

At step 808, the classifiers vote on the heart rate, arterial blood pressure and other extracted features of the patient. In particular, the record of the patient received at 802 may correspond to a patient with an unknown serum lactate level, and it is desirable to use the systems and methods described herein to determine the serum lactate level for the patient. The vote aggregator 558 then aggregates the votes to determine the likelihoods of the serum lactate levels of the patient. The voting collection and aggregation process is described in more detail in relation to FIG. 7, and may include the steps of 702-714 to determine a most likely serum lactate level for the patient. The likelihoods and/or most likely serum lactate level for the patient may be displayed to a user such as a clinician over the display renderer 562 within the user interface 560. In some embodiments, the serum lactate level may be classified along a specific threshold. For example, the serum lactate level of a patient may be classified as less than or greater than 2.5 mmol/L. In addition, the display renderer 562 may also display a confidence score representative of a confidence in the predicted diagnosis. In some embodiments, the display renderer may display, by means of an indicator, an indication of the most likely serum lactate level being over a predetermined threshold. In some embodiments, the indicator may include an audible sound that is played if the most likely serum lactate level is above a predetermined threshold.

At step 810, the serum lactate level determined is used to stratify the risk of sepsis of the patient. The serum lactate level may be used to predict hypoperfusion, lung disease and cardiac shock. The estimated serum lactate level may provide some insight into the patient's vulnerability to risk. For example, a serum lactate level of less than 2.5 mmol/L may be classified as 'low risk', a serum lactate level between 2.5 mmol/L and 4 mmol/L may be 'moderate risk' and serum lactate level greater than 4 mmol/L may be classified as 'high risk' for sepsis. In some embodiments, serum lactate measurements of 4 mmol/L or greater may be associated with mortality rates of 38% in patients with infections, whereas serum lactate levels less than 2.5 mmol/L, and serum lactate levels between 2.5 and 4 mmol/L, may be associated with mortality rates of 15% and 25%, respectively. It is obvious to one of skill in the art that the classification of the risk of sepsis based on serum lactate level may be more or less detailed than the example described herein. In some embodiments, the method 800 may stratify the risk of the health of patients that may have something akin to sepsis that may put their health at risk. In some embodiments, the method 800 is also applicable to intraoperative patients, trauma patients or cardiac arrest patients that may experience elevated serum lactate levels without sepsis. In some embodiments branch of a resuscitation protocol may also be generated. The resuscitation protocol may prompt an intervention from a clinician if the serum lactate level increases past a predetermined threshold.

EXAMPLE 1

The following describes an example study in which serum lactate level is estimated using the machine-learning techniques described herein. In this example, the model used to determine the serum lactate level uses quadratic classifiers generated through quadratic discriminant analysis.

The example study begins with preprocessing training data which is then used to train classifiers that are tested and applied to determine serum lactate levels in a patient. The training data includes a set of patient records with time series data of heart rate, arterial blood pressure and serum lactate level. In some embodiments, the heart rate and arterial blood pressure data for each patient may be available over 15 minutes, 20 minutes, 60 minutes and so on. The training stage is used to discover potential correlations between the heart rate, arterial blood pressure and the serum lactate level to train classifiers and formulate a predictive model.

Figure 13:
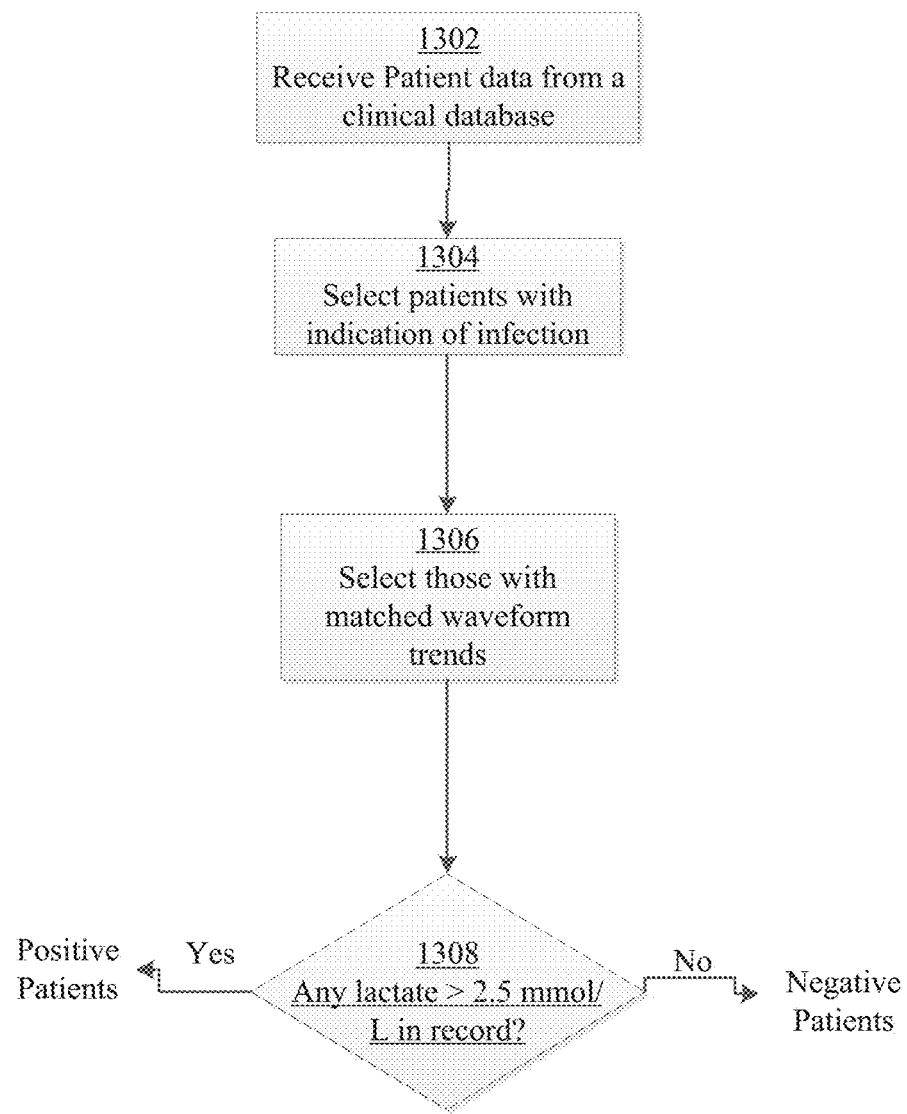
FIG. 13 is a flow diagram of filtering the database for preprocessing training data to train the classifiers, according to an illustrative embodiment.

FIG. 13 is a flowchart of filtering a clinical database for preprocessing training data to train the classifiers as discussed previously in the training process 202. In this example, the database is an instance of the MIMIC II database that includes extensive high resolution waveform data, such as arterial blood pressure and windowed average of heart rate windows derived from electrocardiograms (ECG) (step 1302). In this example, the MIMIC II database contains 32,608 patient records. From the 32,608 patient records in the MIMIC II database, the training stage filters the database to select those patient records that contain an indication of infection, which is based on the presence of an ICD-9 diagnosis codes (step 1304). About 9,708 patient records are filtered from the initial 32,608 patient records. The records are filtered again to obtain 1215 records of patients with matched waveform trends (step 1306). These 1215 records are split into two groups: those who had a lactate reading of at least 2.5 mmol/L in their record (positive class), and those whose lactate measurements were all below 2.5 mmol/L (negative class) (decision block 1308).

In the training stage, the training data is divided into a training set and a testing set. In this example, the 80% of the training input data is classified into a training set and 20% of the training input data is classified into a testing data set. A variety of classifiers are trained on the training set and a receiver operating characteristic (ROC) is generated based on the performance of the classifier on the testing data set.

Figure 9:
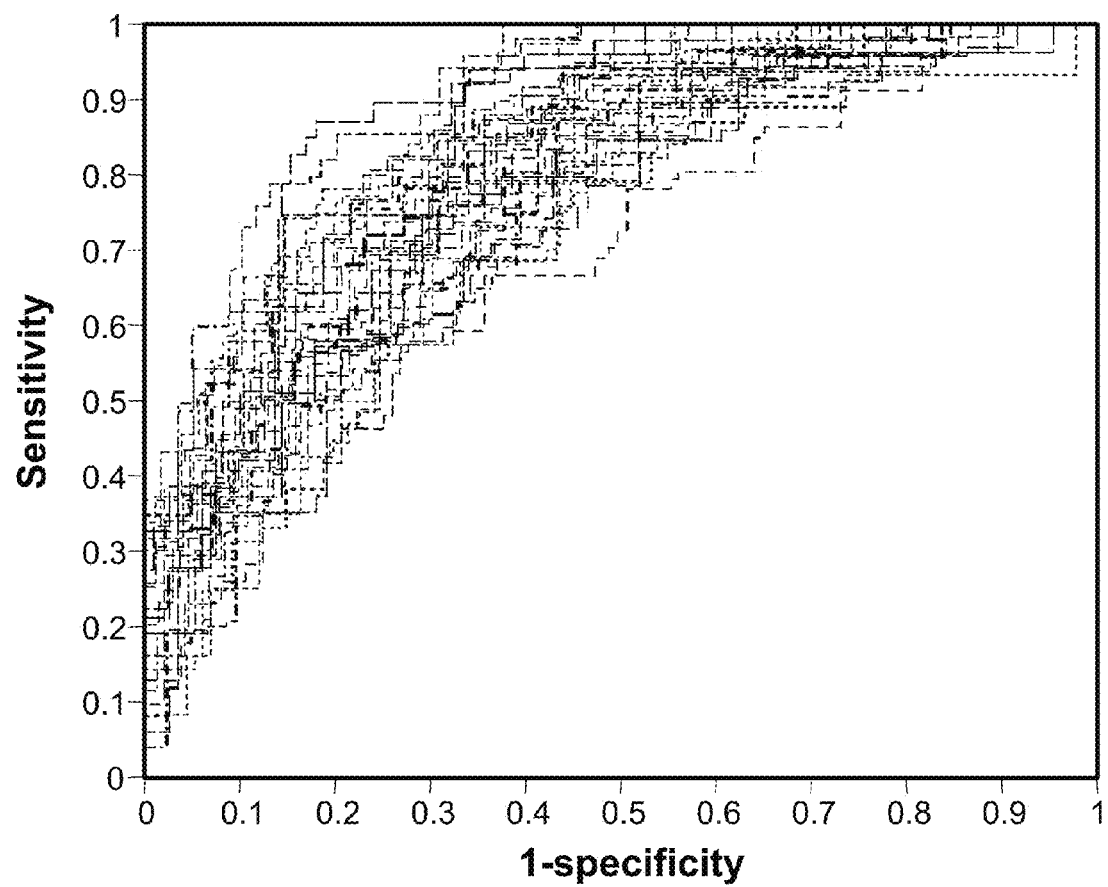
FIG. 9 depicts a performance of a set of 100 classifiers on the testing data, wherein each classifier is trained on a random 80% set of training data, according to an illustrative embodiment.
Figure 10:
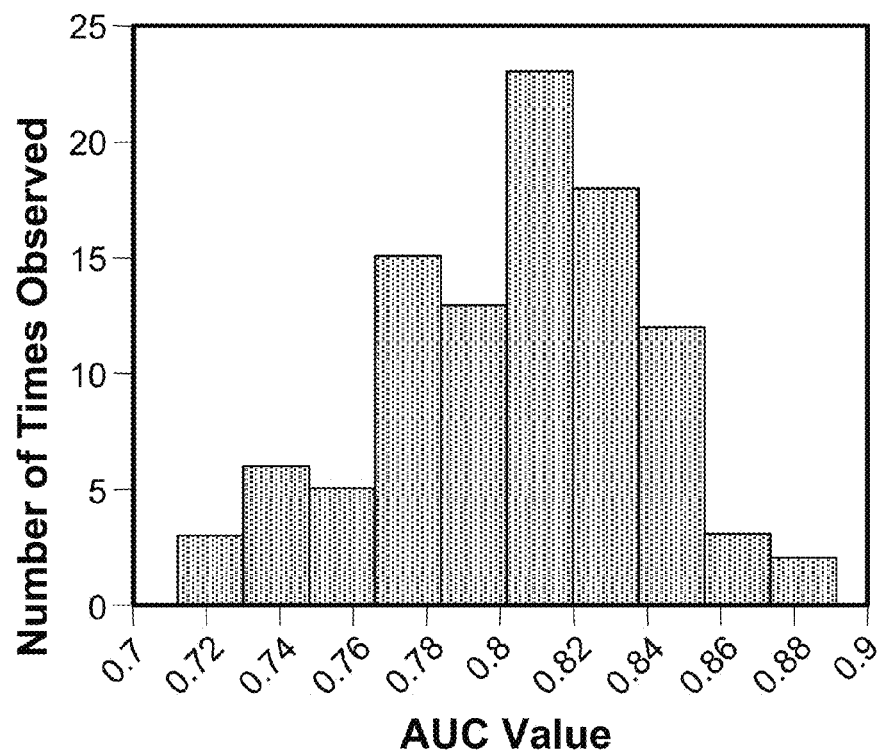
FIG. 10 depicts histograms areas under the receiver operating characteristic curves and equal error rate values for a set of 100 classifiers, according to an illustrative embodiment.
Figure 10:
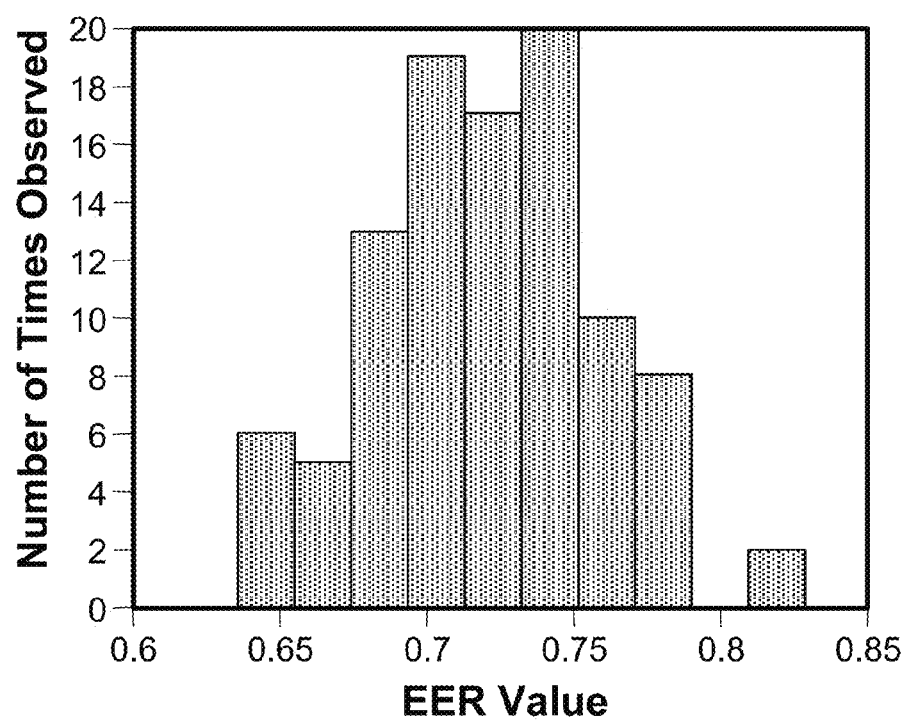

FIG. 9 depicts a performance of a set of 100 classifiers on the testing data, where each classifier is trained on a random 80% set of training data. Each classifier is evaluated using statistics collected over the 100 trials, namely, the area under the curve (AUC) and the equal error rate (EER), which is the point of equal sensitivity and specificity, or equivalently the point for which the false positive rate equals that of a missed detection. FIG. 10 is a histogram depicting the AUC and EER values of the set of 100 classifiers discussed with respect to FIG. 9.

Once all the ROC' s are generated, the best classifier is selected in the testing stage for the application stage. A classifier including an ensemble 100 quadratic discriminant analysis (QDA) voters (or component classifiers) is considered, each trained on a random 70% of the training data (assuming equal priors for the two classes). Each voter fits two maximum likelihood Gaussian models—one to the positive training examples and the other to the negative training examples. Assuming equal priors for the two classes, the likelihood that each test point belongs to the positive class is computed. The ROC curves are produced by variable thresholding of the median posterior probability among the voters that each test point belongs to the positive class.

Figure 11:
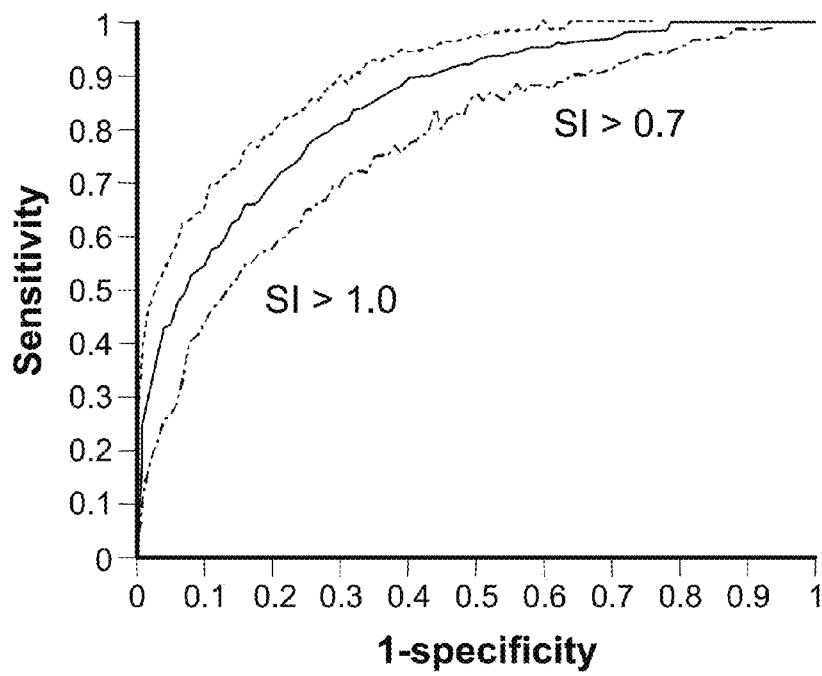
FIG. 11 depicts a median sensitivity value (along with upper and lower quartiles) for each specificity value, for a set of 100 receiver operating characteristic curves associated with classification for serum lactate threshold 2.5 mmol/L, according to an illustrative embodiment.

FIG. 11 depicts the performance of a classifier based on the predetermined threshold of 2.5 mmol/L in comparison with shock index values determined from other parameters extracted from the patient data. FIG. 11 shows the median sensitivity value for each specificity value for the 100 receiver operating characteristic curves as discussed in relation to FIGS. 9 and 10. As is shown in FIG. 11, the value of the serum lactate level determined by applying the classifiers as depicted in the flow diagram of FIG. 8 is more sensitive than using the values of the shock index from derived parameters as explained in Berger, Tony et al. "Shock index and early recognition of sepsis in the emergency department: pilot study." *Western Journal of Emergency Medicine*, 14(2), 168-174. 2013. ("Berger").

Figure 12:
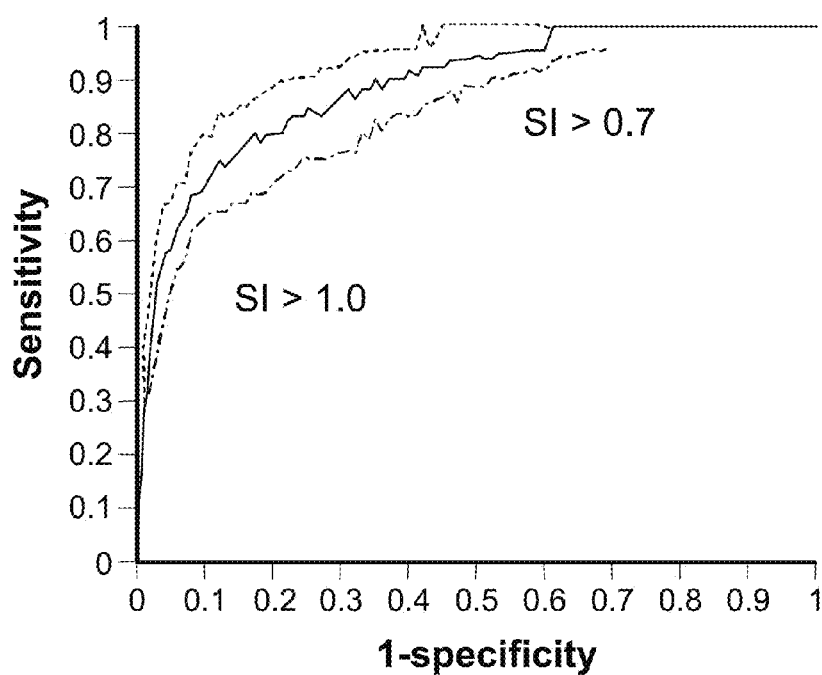
FIG. 12 depicts a median sensitivity value along with upper and lower quartiles) for a set of 100 receiver operating characteristic curves associated with classification for serum lactate threshold 4 mmol/L, according to an illustrative embodiment.

FIG. 12 depicts the performance of the classifier previously discussed in relation to FIGS. 9-11. FIG. 12 is a representation of discriminating serum lactate levels greater than 4 mmol/L from serum lactate levels less than 4 mmol/L. FIG. 12 shows the median sensitivity value for each specificity of the 100 receiver operating characteristic curves as discussed in relation to FIGS. 9-11. As is shown in FIG. 12, the value of the serum lactate level determined by applying the classifiers as depicted in the flow diagram of FIG. 8 is more sensitive than using the values of the shock index from derived parameters as explained in Berger.

In this example study, among the patients with only low lactate measurements in their record, the median age was 70.0 years (median absolute deviation from the median [MAD]: 11.2 years) and in-hospital mortality was 27% among the 61 with high lactate readings, the median age was 63.2 years (MAD: 17.7 years) in-hospital mortality was 43%. For the positive class, the median lactate reading following accepted data frames was 3.4 mmol/L (MAD: 0.7 mmol/L); the median value of all readings recorded in the database for patients with at least one positive frame was 2.3 mmol/L. (MAD: 0.8 mmol/L). For the negative class, these values were both 1.2 mmol/L (MAD: 0.3 mmol/L).

In this example study, the best classifier extracted from the data from the MIMIC II database used the following features: the median systolic blood pressure, the log ratio of the median heart rate over the first two hours to the median heart rate over the last two, the log ratio of median systolic blood pressure over the first two hours to the last two, and the slope term of the robust linear fit to systolic blood pressure. It performed with mean AUC of 0.77, and the mean EER was 0.71. The best QDA-based classifier using only features extracted from the SI depended on SI' s MAD, its log ratio of the median over the first two hours to the mediation over the last two, and the slope of its robust linear fit. Its mean AUC was 0.72 and mean EER was 0.66. The best decision tree ensemble classifier achieved a mean AUC of 0.82 and EER of 0.73 using 25 features, and the classifier with access to only SI-derived features had mean AUC of 0.75 mid EER of 0.70.

This disclosure describes using heart rate and arterial blood pressure to predict a serum lactate level for a patient. However, one of skill in the art will understand that the serum lactate level may be associated with a different set of continuously monitored parameters derived from blood-gas tests or tests of tissue-specific fluids such as gastrointestinal mucosal pH, central venous-to-arterial difference in carbon dioxide tension and its ratio with the arterial-to-venous oxygen content difference, arterial difference of carbon dioxide tension, measures obtained from perfusion scanning, or any suitable combination thereof. In some embodiments, the system and methods described in this disclosure may be used to measure hypoperfusion in a patient with an indicator different from the serum lactate level. In some embodiments, systems and methods described in this disclosure may be used to predict serum lactate level or related clinical quantities related to hypoperfusion at a number of times, wherein the prediction is not real-time or causal. In some embodiments, the machine learning technique used to generate a predictive model may be a regression used to estimate the posterior probability of a hidden state like hypoperfusion or serum lactate level, for example. In some embodiments, a sum-product message passing may be used to estimate the posterior probability of a hidden state like hypoperfusion or serum lactate level, for example.

While various embodiments of the present disclosure have been shown and described herein, such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

The invention claimed is:

1. A method to estimate a patient's serum lactate level, comprising:
   measuring arterial blood pressure and heart rate from the patient; computing estimates of one or more cardiovascular parameters from the measured arterial blood pressure and heart rate;
   extracting one or more static parameters from history associated with the patient;

providing one or more classifiers that have been trained on a training data set obtained from a group comprising patients that are not the patient, the training data set including:
    a reference set of arterial blood pressure, heart rate, and serum lactate levels recorded from the group,
    estimates of one or more cardiovascular parameters from the reference set that correspond to the one or more cardiovascular parameters estimated from the measured arterial blood pressure and heart rate of the patient, and
    one or more static parameters extracted from histories associated with the group that correspond to the one or more static parameters extracted from the history associated with the patient; and
using, at an application stage, the one or more classifiers and one or more of the measured arterial blood pressure and heart rate, the estimates of the one or more cardiovascular parameters from the measured blood pressure and heart rate from the patient, and the one or more static parameters extracted from the history associated with the patient to estimate the serum lactate level of the patient,
wherein the one or more classifiers has been trained at least in part on one or more selected subsets of the training data set, the selected subsets formed at least in part based on the one or more static parameters extracted from the history associated with the patient.

2. The method of claim 1, wherein a risk of sepsis is assigned to the patient depending on the estimated serum lactate level.

3. The method of claim 1, wherein the one or more cardiovascular parameters estimated from the measured arterial blood pressure and heart rate of the patient include at least one of a total peripheral resistance, cardiac output, and stroke volume.

4. The method of claim 1, wherein the history associated with the patient includes demographic information and one or more lab values.

5. The method of claim 1, wherein the selected subsets of the training data set comprise patients with similar history.

6. The method of claim 1, wherein the arterial blood pressure and heart rate are determined from real-time wave forms.

7. The method of claim 1, wherein an alarm is generated if the estimated serum lactate level of the patient crosses a predetermined threshold.

8. The method of claim 1, wherein a classifier from the one or more classifiers is selected to estimate serum lactate level for a patient, wherein the selected classifier is based on a set of features including a median systolic blood pressure and a log-ratio that compares a first median heart rate for a length of time as measured at a beginning of a measurement and a second median heart rate for the length of time as measured at an end of the measurement.

9. The method of claim 1, wherein at least one of the one or more classifiers has a high median area under the curve value and/or a high equal error rate sensitivity in comparison to other classifiers in the one or more classifiers.

10. The method of claim 1, wherein the estimate of the patient's serum lactate level is an estimate of the patient's current serum lactate level.

11. The method of claim 1, wherein the estimate of the patient's serum lactate level is a prediction of a future serum lactate level of the patient.

12. The method of claim 1, wherein the estimate of the patient's serum lactate level is an estimate of the past serum lactate level of the patient.

13. A system to estimate a patient's serum lactate level, the system comprising at least one processor configured to:
    measure arterial blood pressure and heart rate from the patient;
    compute estimates of one or more cardiovascular parameters from the measured arterial blood pressure and heart rate;
    extract one or more static parameters from history associated with the patient;
    provide one or more classifiers that have been trained on a training data set obtained from a group comprising patients that are not the patient, the training data set including:
        a reference set of arterial blood pressure, heart rate, and serum lactate levels recorded from the group,
        estimates of one or more cardiovascular parameters from the reference set that correspond to the one or more cardiovascular parameters estimated from the measured arterial blood pressure and heart rate of the patient, and
        one or more static parameters extracted from histories associated with the group that correspond to the one or more static parameters extracted from the history associated with the patient; and
    use, at an application stage, the one or more classifiers and one or more of the measured arterial blood pressure and heart rate, the estimates of the one or more cardiovascular parameters from the measured blood pressure and heart rate from the patient, and the one or more static parameters extracted from the history associated with the patient to estimate the serum lactate level of the patient,
wherein the one or more classifiers has been trained at least in part on one or more selected subsets of the training data, the selected subsets formed at least in part based on the one or more static parameters extracted from the history associated with the patient.

14. The system of claim 13, wherein a risk of sepsis is assigned to the patient depending on the estimated serum lactate level.

15. The system of claim 13, wherein the one or more cardiovascular parameters estimated from the measured arterial blood pressure and heart rate of the patient include at least one of a total peripheral resistance, cardiac output, and stroke volume.

16. The system of claim 13, wherein the history associated with the patient includes demographic information and one or more lab values.

17. The system of claim 13, wherein the selected subsets of the training data set comprise patients with similar history.

18. The system of claim 13, wherein the arterial blood pressure and heart rate are determined from real-time wave forms.

19. The system of claim 13, wherein an alarm is generated if the estimated serum lactate level of the patient crosses a predetermined threshold.

20. The system of claim 13, wherein a classifier from the one or more classifiers is selected to estimate serum lactate level for a patient, wherein the selected classifier is based on a set of features including a median systolic blood pressure and a log-ratio that compares a first median heart rate for a length of time as measured at a beginning of a measurement and a second median heart rate for the length of time as measured at an end of the measurement.

21. The system of claim 13, wherein at least one of the one or more classifiers has a high median area under the curve value and/or a high equal error rate sensitivity in comparison to other classifiers in the one or more classifiers.

22. The system of claim 13, wherein the estimate of the patient's serum lactate level is an estimate of the patient's current serum lactate level.

23. The system of claim 13, wherein the estimate of the patient's serum lactate level is a prediction of a future serum lactate level of the patient.

24. The system of claim 13, wherein the estimate of the patient's serum lactate level is an estimate of the past serum lactate level of the patient.

25. A method for treating a patient, comprising:
performing an intervention on a patient if an estimated serum lactate level of the patient is increased past a predetermined threshold, wherein the estimated serum lactate level is determined based at least in part on:
measurement of arterial blood pressure and heart rate from the patient,
a computation of estimates of one or more cardiovascular parameters from the measured arterial blood pressure and heart rate,
extraction of one or more static parameters from history associated with the patient, and
use of, at an application stage, one or more classifiers and one or more of the measured arterial blood pressure and heart rate, the estimates of the one or more cardiovascular parameters from the measured blood pressure and heart rate from the patient, and the one or more static parameters extracted from the history associated with the patient;
wherein:
the one or more classifiers have been trained on a training data set obtained from a group comprising patients that are not the patient, the training data set including:
a reference set of arterial blood pressure, heart rate, and serum lactate levels recorded from the group,
estimates of one or more cardiovascular parameters from the reference set that correspond to the those estimated from the measured arterial blood pressure and heart rate of the patient, and
one or more static parameters extracted from histories associated with the group that correspond to those extracted from the history associated with the patient; and
the one or more classifiers have been trained at least in part on one or more selected subsets of the training data, the subsets formed at least in part based on the one or more static parameters extracted from the history associated with the patient.

* * * * *